(12) United States Patent
Ormonde et al.

(10) Patent No.: US 11,357,878 B2
(45) Date of Patent: Jun. 14, 2022

(54) APPARATUS, PROBE ASSEMBLY AND METHODS FOR TREATING CONTAINERS

(71) Applicant: KAIATECH, INC., Fremont, CA (US)

(72) Inventors: Gabriel Ormonde, Lathrop, CA (US); Ronald Stevens, Pleasanton, CA (US); Kenneth Twain, Oakland, CA (US); Craig Galloway, Hillsborough, NC (US); Michelle (Meng) Shi, San Jose, CA (US); James Mitchener, Danville, CA (US)

(73) Assignee: KAIATECH, INC., Fremont, CA (US)

( * ) Notice: Subject to any disclaimer, the term of this patent is extended or adjusted under 35 U.S.C. 154(b) by 0 days.

(21) Appl. No.: 17/139,036

(22) Filed: Dec. 31, 2020

(65) Prior Publication Data

US 2021/0121590 A1    Apr. 29, 2021

Related U.S. Application Data

(63) Continuation of application No. PCT/IB2020/053101, filed on Apr. 1, 2020.
(Continued)

(51) Int. Cl.
*H01J 37/32* (2006.01)
*A61L 2/14* (2006.01)
(Continued)

(52) U.S. Cl.
CPC .............. *A61L 2/14* (2013.01); *A61L 2/26* (2013.01); *B08B 7/0035* (2013.01); *B08B 9/20* (2013.01);
(Continued)

(58) Field of Classification Search
None
See application file for complete search history.

(56) References Cited

U.S. PATENT DOCUMENTS 3,442,686 A    5/1969  Jones
5,565,248 A    10/1996 Plester et al.
(Continued)

FOREIGN PATENT DOCUMENTS

| EP | 0665304 A1 | 8/1995 |
| JP | H05106053 A | 4/1993 |
| JP | 2006236697 A * | 9/2006 |

OTHER PUBLICATIONS

International Search Report from PCT Application No. PCT/IB20/53101, dated Jul. 28, 2020.

*Primary Examiner* — Karla A Moore
(74) *Attorney, Agent, or Firm* — Budzyn IP Law, LLC (57) ABSTRACT

The invention provides an apparatus for treating surfaces of a container. The apparatus comprises an openable reaction chamber housing, an exhaust escapement and an electrode assembly. The electrode assembly comprises a probe assembly coupled with a power source, the probe assembly comprising an elongate wand body, and a helically configured primary electrode and a helically configured counter electrode disposed about an outer circumferential surface of the wand body in an alternating helical configuration. The elongate wand body has a fluid passageway defined therewithin, and one or more outlet openings that are formed on an outer circumferential surface of the wand body and that extend inward through said outer circumferential surface and upto the fluid passageway. One or both of the primary electrode and the counter electrode may be energizable by the power source.

16 Claims, 8 Drawing Sheets

Related U.S. Application Data (60) Provisional application No. 62/828,620, filed on Apr. 3, 2019.

(51) Int. Cl.
- *A61L 2/26* (2006.01)
- *B08B 7/00* (2006.01)
- *B08B 9/20* (2006.01)
- *C23C 16/44* (2006.01)
- *C23C 16/455* (2006.01)
- *C23C 16/50* (2006.01)

(52) U.S. Cl.
CPC .... *C23C 16/4412* (2013.01); *C23C 16/45578* (2013.01); *C23C 16/50* (2013.01); *H01J 37/3244* (2013.01); *H01J 37/32394* (2013.01); *H01J 37/32541* (2013.01); *H01J 37/32834* (2013.01); *A61L 2202/11* (2013.01); *A61L 2202/122* (2013.01); *A61L 2202/23* (2013.01)

(56) References Cited

U.S. PATENT DOCUMENTS

| | | | |
|---|---|---|---|
| 5,679,412 | A | 10/1997 | Kuehnle et al. |
| 5,704,983 | A | 1/1998 | Thomas et al. |
| 5,728,149 | A | 3/1998 | Laske et al. |
| 6,112,695 | A | 9/2000 | Felts |
| 7,387,081 | B2 | 6/2008 | David et al. |
| 10,081,864 | B2 | 9/2018 | Stevens et al. |
| 2002/0007793 | A1* | 1/2002 | Sakai ............ C23C 16/24 118/723 E |
| 2007/0005053 | A1 | 1/2007 | Dando |
| 2010/0064971 | A1* | 3/2010 | Lee ............ C23C 16/50 118/723 E |
| 2010/0096393 | A1 | 4/2010 | Asahara et al. |
| 2010/0215871 | A1* | 8/2010 | Lee ............ C23C 16/06 427/569 |
| 2012/0231182 | A1* | 9/2012 | Stevens ............ H01J 37/32394 427/576 |

* cited by examiner

APPARATUS, PROBE ASSEMBLY AND METHODS FOR TREATING CONTAINERS

FIELD OF THE INVENTION

The present invention relates to the field of treating containers, and in particular provides apparatuses, probe assemblies and methods for treating containers for sterilization, application of coatings or thin film linings, or for any other treatment objective.

BACKGROUND

The packaging industry utilizes three dimensional formed containers for packaging of food and beverage products, pharmaceuticals, nutritional supplements, medical devices, supplies, containment vessels, household products, auto lubricants, and other products. These containers can have weak properties that limit their use and usable lifecycle.

For example, for plastic containers the shelf life of a product may depend on several properties including oxygen, carbon dioxide, and water vapor transmission rates through the packaging container as well as chemical reactivity between the packaging and its contents. Alternately, a plastic container for pesticides or chemicals may absorb the contents, rendering the container as hazardous waste because a simple rinsing of the container does not remove the hazard. Additional examples include metal and paper composite containers. For metal containers, the conventional barrier applied to prevent corrosion to the container and metal contamination to the contents is an epoxy that contains BPA (Bisphenol-A) now known to have adverse health effects. In an attempt to ban BPA in certain regions, substitute epoxies have been developed only to result in similar adverse health effects. In the case of paper composite materials, to ensure their viability to contain liquids, the paper is generally mixed or treated with plastic or wax which renders them limited in recycling potential. Glass (SiOx based) is considered the benchmark material for providing content integrity. However, glass containers are costly to fabricate, use large energy resources, require sterilization, and are cumbersome in handling and shipping due to the fragile nature and weight of glass.

The packaging industries has developed equipment for applying appropriate barriers and coatings to two-dimensional flat roll materials (i.e. flexible packaging in plastics, metals, and paper). For example, stacked-barrier solutions for polymers using vacuum evaporation and spin-on techniques have been well documented since 1964 (Jones U.S. Pat. No. 3,442,686). Since, solutions have been introduced for rigid three-dimensional plastic containers and that use plasma energy to deposit very thin barriers of SiOx as well as other acceptable materials (depending on the intended use) such as: SiOxCy, SiNx, SiOxNy, $Al_2O_3$, or DLC (diamond like carbon) on the interior of plastic containers to obtain the barrier properties that address weaknesses in conventional containers (Kuehnle, et al. U.S. Pat. No. 5,679, 412). Additionally, such systems and processes can treat container surfaces for other reasons, such as, sterilization, surface texturizing, creating hydrophobic or hydrophilic properties, screen printing adhesion of inks, and others.

Generally, the systems in use have been configured using either microwave energy communicating with a ground electrode inside the container interior; or, using radio frequency (RF) energy with an electrode outside the container and another electrode inside the container; or using direct current (DC) power connected to one or both electrodes. These implementations require careful pressure control and a seal between the inside and outside of the container which can be problematic in a production environment.

In some prior art systems (for example US 2010/0096393), the container being treated is placed within a cavity having an external electrode covering an outer circumference of the container, and an internal electrode inserted into the container, and a means for delivering precursor materials into the container. An electric field, electromagnetic field, electrostatic field or radio frequency (RF) field applied across the external electrode and internal electrode causes the precursor materials to disassociate and to form plasma, which plasma is deposited onto the surfaces (for example an internal surface) of the container to form a film or coating. This configuration has multiple drawbacks—including that (i) using it to treat metal containers results in undesirable sparking or arcing, and (ii) using it to treat plastic containers has been found to have detrimental effects on the plastic materials of the container (for example due to heating caused by the field generated between the internal and external electrodes).

Other embodiments of electrode assemblies that enable RF and microwave energy integration have also been developed (see for example, U.S. Pat. Nos. 5,565,248, 6,112,695 and 5,704,983). As in the case of US 2010/0096393, these systems utilize a configuration where energy is directed from the outside of the container to the inside (through the container wall), with the accompanying drawbacks discussed above.

More recently, a system has been developed that further simplifies the ignition and containment of the plasma from using electrical communication on either side of the container, to that which confines the plasma within the interior of the container (Stevens, et al. U.S. Pat. No. 10,081,864). This system relies on an elongated probe type component configured to be inserted into a container, the probe having a co-annular arrangement of two or more electrodes, a fluid passageway formed therebetween and an outlet for the fluid passageway at one end of the elongated probe. Precursor materials are passed through the fluid passageway, and as a result of an electric, electromagnetic, electrostatic or RF field applied across the fluid passageway, results in plasma generation—which plasma is delivered onto internal surfaces of the container from the probe outlet. However, it has been found that for high aspect ratio (height:diameter ratio) containers, this implementation results in non-uniform plasma deposition along the central long axis of the container, resulting in non-uniform thickness films.

There is accordingly a need for an apparatus and an electrode assembly that combines favorable gas flow characteristics with plasma density uniformity in the radial direction, and controlled deposition uniformity in the axial direction, to obtain a uniform thin-film coating.

SUMMARY

The present invention provides apparatuses, electrode assemblies and methods for treatment of container surfaces.

In an embodiment, the invention provides an assembly combining opposing electrodes physically wrapped around a gas applicator that results in said assembly being inserted into the interior diameter of a container while simultaneously achieving both uniform plasma density and gas flow for a conformal deposition of thin films on the interior surfaces of the rigid container walls.

In a further embodiment, the invention provides that the electrodes and gas applicator are separate components that allow the disassembly, cleaning, and reassembly of the components, or the substitution of any of the individual components to reduce consumable (or replacement) costs when used in a production environment.

The electrode assembly comprises three essential elements for the electrodes and gas applicator—one each of two electrodes made of conductive metal wire or rod(s) or similar lengthwise extrusion that can be shaped around a central gas applicator; and, the central gas applicator that is a single-ended tube shape with gas escapement(s) along it's axial and/or radial direction whereas the gas escapements are located at the end and/or between the electrodes in the radial direction. The invention may additionally involve a fourth part that the electrodes and gas applicator mount into, which allows for the vacuum/atmospheric mount interface and provides a gas path to direct the process gas to the inner hollow of the gas applicator. In a preferred embodiment, the single-ended tube shape with gas escapement(s) is achieved using a removable tip that can be changed to provide more or less gas escapements.

In an embodiment, the invention provides an apparatus for treating surfaces of a container. The apparatus comprises an openable reaction chamber housing, an exhaust escapement and an electrode assembly.

The openable reaction chamber housing is configured to define an interior vacuum chamber configured to house a container to be treated. The exhaust escapement is configured to permit gases to exit the interior vacuum chamber.

The electrode assembly is configured for coupling with a power source, and positioned at least partially within the interior vacuum chamber, such that a part of the electrode assembly is positioned within an interior cavity of the container housed within the interior vacuum chamber.

The electrode assembly comprises a probe assembly coupled with the power source, the probe assembly comprising an elongate wand body, a helically configured primary electrode and a helically configured counter electrode.

The elongate wand body has a fluid passageway defined therewithin, and one or more outlet openings that are formed on an outer circumferential surface of the wand body and that extend inward through said outer circumferential surface and upto the fluid passageway. The one or more outlet openings enable one or more precursor gases passing through said fluid passageway to enter the interior vacuum chamber or the interior cavity of the container housed within the interior vacuum chamber.

The helically configured primary electrode is disposed about the outer circumferential surface of the wand body and has a first plurality of turns, wherein one or more of the first plurality of turns is spaced apart from each immediately adjacent turn within the first plurality of turns.

The helically configured counter electrode is disposed about the outer circumferential surface of the wand body and has a second plurality of turns, wherein one or more of the second plurality of turns is spaced apart from each immediately adjacent turn within the second plurality of turns.

The primary electrode and the counter electrode may be disposed about the outer circumferential surface of the wand body in an alternating helical configuration such that one or more turns of the primary electrode are formed immediately adjacent and spaced apart from one or more turns of the counter electrode. Additionally, one or both of the primary electrode and the counter electrode are energizable by the power source.

In a further embodiment of the apparatus, the fluid passageway within the wand body is coupled with an inlet manifold configured to deliver the one or more precursor gases from a precursor gas source into the fluid passageway.

In another embodiment of the apparatus, at least a part of the primary electrode and a part of the counter electrode are spaced substantially parallel to each other and are each respectively disposed about the outer circumferential surface of the wand body in a helical configuration.

In a particular embodiment of the apparatus, a plurality of individual turns of the primary electrode are formed immediately adjacent to and spaced apart from a respective plurality of individual turns of the counter electrode.

The apparatus may be configured such that the part of the primary electrode that is disposed about the outer circumferential surface of the wand body in a helical configuration has a constant pitch across the wand body. In another embodiment, the part of the counter electrode that is disposed about the outer circumferential surface of the wand body in a helical configuration has a constant pitch across the wand body.

The apparatus may be configured such that (i) the part of the primary electrode that is disposed about the outer circumferential surface of the wand body in a helical configuration has a varying pitch across the wand body, or (ii) the part of the counter electrode that is disposed about the outer circumferential surface of the wand body in a helical configuration has a varying pitch across the wand body.

In a specific embodiment of the apparatus, one or more of the outlet openings are positioned on the outer circumferential surface of the wand body between adjacently positioned turns of the primary electrode and the counter electrode.

In another embodiment of the apparatus (i) the primary electrode is one of an anode or a cathode or a ground, and the counter electrode is another of the anode or the cathode or the ground, or (ii) the primary electrode and the counter electrode respectively have different or alternating polarities.

In one embodiment of the apparatus as claimed in claim 1, the wand body is formed from an electrically insulative material, and the primary electrode and counter electrode are formed from one or more electrically conductive materials.

The apparatus may be configured such that one or both of the primary electrode and the counter electrode each comprise (i) any one of a flat wire electrode, round wire electrode, flat tube electrode, or round tube electrode or other electrode that is wound or otherwise affixed in a helical arrangement about the wand body, or (ii) an electrode that is integrally, additively, depositively or otherwise formed in a helical arrangement upon the outer circumferential surface of the wand body.

In another embodiment, the invention comprises an electrode assembly for an apparatus for treating surfaces of a container. The apparatus comprises the electrode assembly, an openable reaction chamber housing defining an interior vacuum chamber configured to house a container to be treated, and an exhaust escapement configured to permit gases to exit the interior vacuum chamber. The electrode assembly comprises a probe assembly coupled with a power source. The probe assembly comprises an elongate wand, a helically configured primary electrode and a helically configured secondary electrode.

The elongate wand body of the probe assembly is configured to have a fluid passageway defined therewithin, and one or more outlet openings that are formed on an outer circumferential surface of the wand body and that extend inward through said outer circumferential surface and upto the fluid passageway. The one or more outlet openings enable one or more precursor gases passing through said fluid passageway to enter the interior vacuum chamber or the interior cavity of the container housed within the interior vacuum chamber.

The helically configured primary electrode of the probe assembly is disposed about the outer circumferential surface of the wand body and having a first plurality of turns, wherein one or more of the first plurality of turns is spaced apart from each immediately adjacent turn within the first plurality of turns.

The helically configured counter electrode of the probe assembly is disposed about the outer circumferential surface of the wand body and having a second plurality of turns, wherein one or more of the second plurality of turns is spaced apart from each immediately adjacent turn within the second plurality of turns.

In an embodiment of the probe assembly, the primary electrode and the counter electrode are disposed about the outer circumferential surface of the wand body in an alternating helical configuration such that one or more turns of the primary electrode are formed immediately adjacent and spaced apart from one or more turns of the counter electrode. Additionally, one or both of the primary electrode and the counter electrode are energizable by the power source;

The electrode assembly may be positioned at least partially within the interior vacuum chamber such that a part of the wand body is positioned within an interior cavity of the container housed within the interior vacuum chamber, In an embodiment of the electrode assembly, the fluid passageway within the wand body is coupled with an inlet manifold configured to deliver the one or more precursor gases from a precursor gas source into the fluid passageway.

In another embodiment of the electrode assembly, at least a part of the primary electrode and a part of the counter electrode are spaced substantially parallel to each other and are each respectively disposed about the outer circumferential surface of the wand body in a helical configuration.

The electrode assembly may be configured such that (i) the part of the primary electrode that is disposed about the outer circumferential surface of the wand body in a helical configuration has a constant pitch across the wand body, or (ii) the part of the counter electrode that is disposed about the outer circumferential surface of the wand body in a helical configuration has a constant pitch across the wand body, or (iii) the part of the primary electrode that is disposed about the outer circumferential surface of the wand body in a helical configuration has a varying pitch across the wand body, or (iv) the part of the counter electrode that is disposed about the outer circumferential surface of the wand body in a helical configuration has a varying pitch across the wand body.

In an embodiment of the electrode assembly, one or more of the outlet openings are positioned on the outer circumferential surface of the wand body between adjacently positioned turns of the primary electrode and the counter electrode.

In another embodiment of the electrode assembly, the wand body is formed from an electrically insulative material, and the primary electrode and counter electrode are formed from one or more electrically conductive materials.

The electrode assembly may be configured such that one or both of the primary electrode and the counter electrode each comprise (i) any one of a flat wire electrode, round wire electrode, flat tube electrode, or round tube electrode or other electrode that is wound or otherwise affixed in a helical arrangement about the wand body, or (ii) an electrode that is integrally, additively, depositively or otherwise formed in a helical arrangement upon the outer circumferential surface of the wand body.

In an embodiment, the invention provides a method for manufacturing a probe assembly for an apparatus for treating surfaces of a container. The apparatus comprises an electrode assembly, an openable reaction chamber housing defining an interior vacuum chamber configured to house a container to be treated, and an exhaust escapement configured to permit gases to exit the interior vacuum chamber. The electrode assembly comprises the probe assembly coupled with a power source. The method of the present invention comprises the steps of (i) providing an elongate wand body having a fluid passageway defined therewithin, the elongate wand body having one or more outlet openings that are formed on an outer circumferential surface of the wand body and that extend inward through said outer circumferential surface and upto the fluid passageway, (ii) disposing a helically configured primary electrode about the outer circumferential surface of the wand body and having a first plurality of turns, wherein one or more of the first plurality of turns is spaced apart from each immediately adjacent turn within the first plurality of turns, (iii) disposing a helically configured counter electrode disposed about the outer circumferential surface of the wand body and having a second plurality of turns, wherein one or more of the second plurality of turns is spaced apart from each immediately adjacent turn within the second plurality of turns, and (iv) providing on each of the primary electrode and the counter electrode one or more electrical connectors for connecting one or both of the said electrodes to a power source.

In an embodiment of the method, the primary electrode and the counter electrode are disposed about the outer circumferential surface of the wand body in an alternating helical configuration such that one or more turns of the primary electrode are formed immediately adjacent and spaced apart from one or more turns of the counter electrode.

In another embodiment of the method, disposing any one of the helically configured primary electrode or the helically configured counter electrode about the outer circumferential surface of the wand body comprises (i) winding or otherwise affixing any one of a flat wire electrode, round wire electrode, flat tube electrode, or round tube electrode or other electrode that is in a helical arrangement about the wand body, or (ii) integrally, additively, depositively or otherwise forming an electrode in a helical arrangement upon the outer circumferential surface of the wand body.

In a further embodiment of the method (i) disposing the part of the primary electrode about the outer circumferential surface of the wand body in a helical configuration comprises disposing said part of the primary electrode about the outer circumferential surface of the wand body with a constant pitch across the wand body, or (ii) disposing the part of the counter electrode about the outer circumferential surface of the wand body in a helical configuration comprises disposing said part of the counter electrode about the outer circumferential surface of the wand body with a constant pitch across the wand body, or (iii) disposing the part of the primary electrode about the outer circumferential surface of the wand body in a helical configuration comprises disposing said part of the primary electrode about the outer circumferential surface of the wand body with a varying pitch across the wand body, or (iv) disposing the part of the counter electrode about the outer circumferential surface of the wand body in a helical configuration comprises disposing said part of the counter electrode about the outer circumferential surface of the wand body with a varying pitch across the wand body.

These and other embodiments are discussed in more detail in the following detailed description.

DETAILED DESCRIPTION OF THE INVENTION

Figure 1:
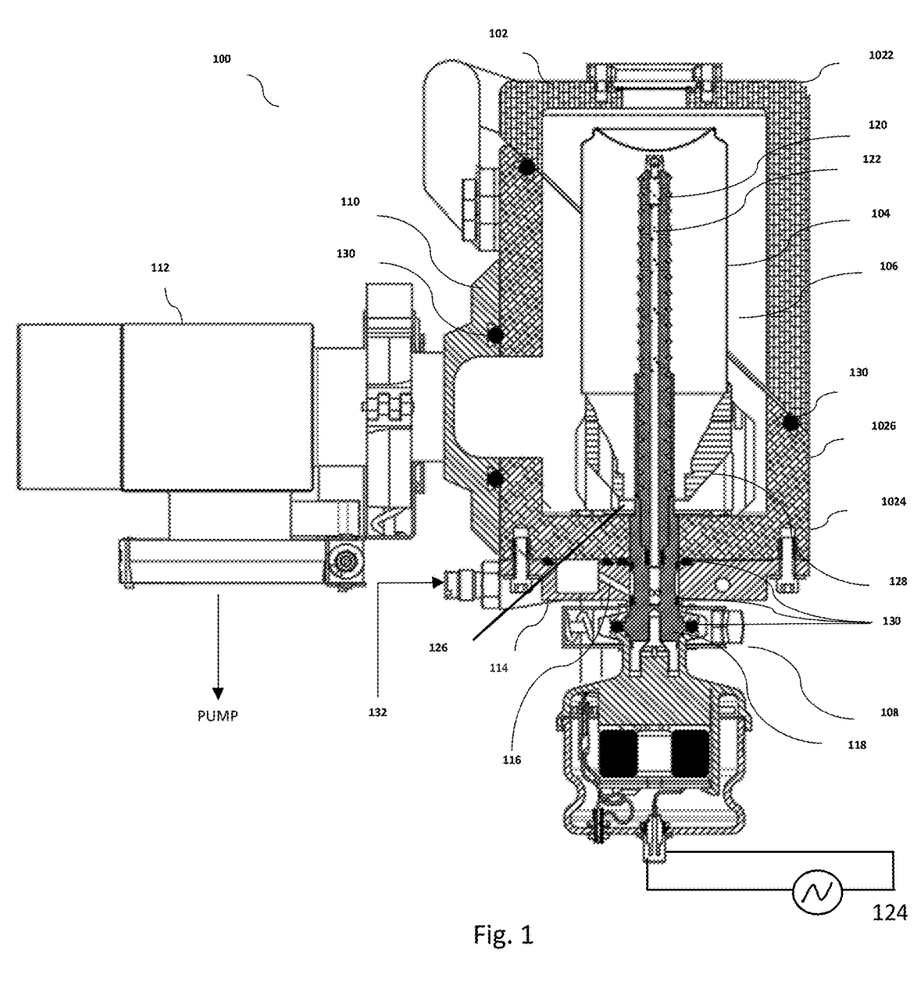
FIG. 1 is a partial illustration of a plasma treatment system in accordance with the present invention.

FIG. 1 is a partial illustration of a system for plasma treatment of surfaces, including without limitation, any of paper, plastic, or metal containers where plasma enhanced chemical vapor is used to etch and/or deposit on the interior walls of the container.

FIG. 1 illustrates an apparatus 100 for plasma treatment of surfaces in accordance with the teachings of the present invention. Apparatus 100 includes a closed reaction chamber housing 102 having a removable or openable upper surface 1022 (for example an upper lid), and a base portion comprising lower surface 1024 and sidewalls 1026, which together form an interior chamber 106. Interior chamber 106 is configured and/or sized to house a container 104 for the purposes of treating one or more surfaces of said container 104.

The apparatus 100 additionally includes at least an electrode assembly 108 that is configured to provide an outlet for precursor gas(es) within a fluid passageway defined within electrode assembly 108 to pass into interior chamber 106, and which is further configured to be energized by application of power from a power source or power supply.

For the purposes of the description concerning FIG. 1, as well as any of the subsequent FIGS. 2A to 5 herein, it would be understood that references to a 'power source' or 'power supply' shall mean a power source or power supply configured to output power at any one or more frequencies within the electromagnetic spectrum, including without limitation any of high frequency power, mid frequency power, low frequency power source, radio frequency (RF) power, microwave frequency power and/or direct current (DC) power.

The precursor gas(es) is electrically excited by energy from the electrode assembly 108, and disassociates into a plasma comprising ions, radicals, and non-radical neutral species. The ions and radicals recombine as a result of collisions with each other and with surrounding surfaces—resulting in the formation of a film that is physically deposited on surfaces of container 104. Electrode assembly 108 includes at least a probe assembly 118. Probe assembly 118 comprises an elongated wand body 120 having a fluid passageway 122 defined there within, and one or more outlet openings that permit for fluid or gas passing through fluid passageway 122 to enter interior chamber 106.

The apparatus 100 additionally includes an exhaust manifold 110 configured to provide an exhaust escapement through which gases may leave interior chamber 106 and through which interior chamber 106 may be evacuated. Exhaust manifold 106 is mounted on a side or to the rear of interior chamber 106 and may be connected to an isolation valve 112 which in turn leads to a pressure control valve and vacuum pump (not shown).

The apparatus 100 includes an inlet manifold 114 configured so that gas(es) comprising precursor materials enters inlet manifold 114 through inlet 132, and passes into fluid passageway 122 within wand body 120 of probe assembly 118 via a flow path 116, such that the gas(es) flows up through the probe assembly 118 and out of holes or outlet openings provided on wand body 120. As discussed in more detail below, the one or more holes or outlet openings provided on wand body 120 may be located between a plurality of electrodes disposed about an outer surface of wand body 120, such that precursor gas(es) entering interior chamber 106 through such holes or outlet openings are electrically excited by the energy from the electrode assembly 108, and disassociates into plasma comprising ions and radicals—for deposition onto the surfaces of container 104.

The electrodes within electrode assembly 108 may be energized via power supply 124, causing precursor gas(es) that passes between such electrodes to disassociate into a plasma that remains confined to the interior of the container. The gas(es) exits the container via an annulus 126 formed between an opening in container 104 and electrode assembly 108 and may thereafter exit interior chamber 106 through exhaust escapement 110. The electrode assembly 108 is sized so the annulus 126 has a cross-section escapement area large enough to minimize the pressure difference (i.e. <100 mT) between the inside and outside of interior chamber 106 when 500 sccm of nitrogen flows through the electrode assembly 108 at a chamber pressure of 1 T.

A container support 128 provided within interior chamber 106 presents a base on which container 104 can be positioned for the purposes of the plasma treatment.

The apparatus 100 may additionally include one or more than one o-rings 130 configured and located to provide vacuum seal(s) at the appropriate interfaces between components of apparatus 100.

During operation of the apparatus 100 for treating surfaces of a container, container 104 is inserted into interior chamber 106 by removing or opening upper surface 1022 and inserting container 104 such that container 104 is mounted over and about electrode assembly 108 through an opening in said container 104 i.e. such that at least a part of electrode assembly 108 extends into an interior cavity defined by the container 104. Upper surface 1022 is thereafter replaced to close interior chamber 106. Closed interior chamber 106 forms a vacuum chamber that is sealed from the outside atmosphere using one or more O-ring seals 130. Interior chamber 106 is then evacuated to a desired process pressure through exhaust manifold 110 (that is connected to isolation valve 112) using a pump with a pressure control valve (not shown). Precursor gas(es) is introduced into the inlet manifold 114 at a predetermined flow rate which then proceeds through flow path 116 to and up through fluid passageway 122 within wand body 120 of probe assembly 120—and thereafter the precursor gas(es) exits wand body 120 through holes or outlet openings provided on wand body 120, into the interior of container 104. Upon exiting wand body 120, the gases are excited and disassociated by energy supplied by power source 124 through electrodes within electrode assembly 108—into their more fundamental species which can include ions, radicals, and non-radical neutral species. The ions and radicals recombine as a result of collisions with each other and with surrounding surfaces—resulting in the formation of a film that is physically deposited on surfaces of container 104. Depending on the application, some of the species may deposit on interior surface(s) of the container or etch the interior surface(s) of the container, while the remainder of the gas species, unreacted and effluent, is exhausted through annulus 126 created between the opening in container 104 and the electrode assembly 108. These gases are then exhausted through the exhaust manifold 110 and isolation valve 112 connected to the pump.

The precursor gases for the present invention may comprise any precursor that is suitable for an intended surface treatment. For example, for the application of barrier films for containers, precursors may include a silicon source (such as, but not limited to: silane gas ($SiH_4$), hexamethyldisiloxane HMDSO, hexamethyldisilazane HMDSN, tri s[dimethylamino]silane TDMAS, tetramethoxysilane TMOS, triethoxysilane, or tetraethyloxysilane (TEOS), and/or oxygen gas ($O_2$) to form silicon oxide ($SiO_x$)). To form silicon oxynitride ($SiO_xN_y$) films, a further precursor, a nitrogen source such as ammonia ($NH_3$) gas may be added. For the application of aluminum containing films to containers, precursors may include an aluminum source such as an aluminum alkoxide, trimethylaluminum (TMA) or $AlCl_3$. Additional precursors could be implemented to form other films, provide dopants to tailor the film properties (such as, but not limited to: I/R or UN filtering), provide a diluent gas, provide pretreatments to prepare the container surface, or sterilize the container. He, $N_2$ and Ar are useful as carriers and/or reactant materials for surface preparation or other reasons such as functionalization. Ar is also useful for initial plasma creation.

For the application of sterilization, example precursors include $O_2$, $N_2$, and nitrous oxide ($N_2O$). When oxygen is used as a precursor, the resulting atomic oxygen and ozone sterilizes the container 104. Sterilization is advantageous in many industry uses where organic contamination is of concern, including but not limited to: food & beverage, medical, petroleum, and general containment. For this reason, it is reasonable to expect sterilization can be an advantageous initial step in multistep treatments and deposition and/or post treatment before filling a container.

Figure 2A:
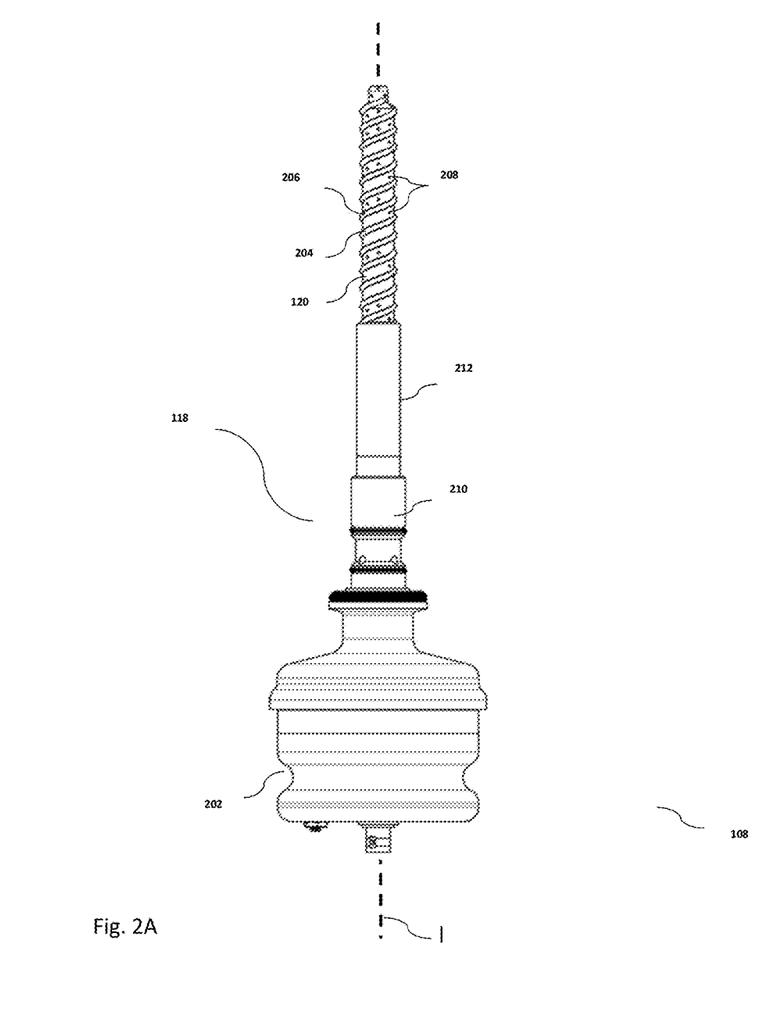
FIGS. 2A and 2B illustrate embodiments of an electrode assembly with a fixed match transformer assembly, in accordance with the present invention.
Figure 2B:
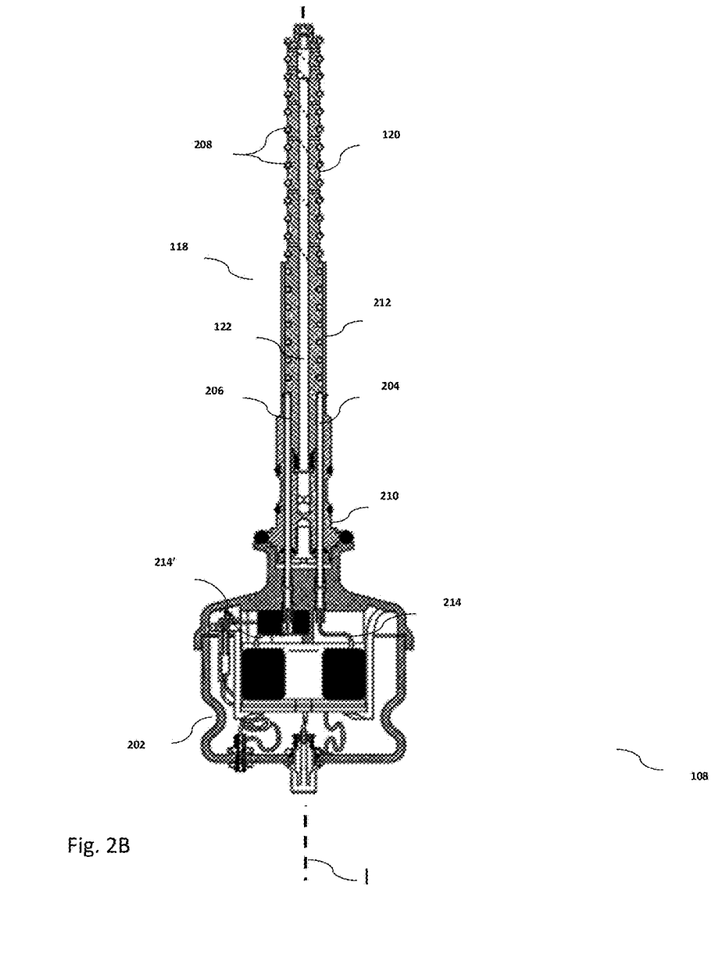

FIG. 2A illustrates an embodiment of electrode assembly 108 comprising a probe assembly 118 coupled with a fixed match transformer assembly 202, while FIG. 2B illustrates a cross-section of the embodiment of probe assembly 118 coupled with the fixed match transformer assembly 202.

As shown in FIG. 2A, probe assembly 118 comprises wand body 120, which may be made of electrical insulative material such as ceramic or plastic. Disposed about or around the external circumference of wand body 120, are a primary electrode 204 (for example, a first electrode connected to any one of a cathode or an anode or a ground) and a counter electrode 206 (for example, a second electrode connected to another of the cathode, anode or ground)—which primary electrode 204 and counter electrode 206 may be connected or coupled with fixed match transformer assembly 202. The primary electrode 204 and/or counter electrode 206 may comprise one or more electrically conductive materials such as metal or carbon. In one embodiment, each of primary electrode 204 and counter electrode 206 may comprise a flexible or pliant electrode that is helically or spirally wrapped or wound about the outer circumference of wand body 120. In a more specific embodiment, each of primary electrode 204 and counter electrode 206 are physically wrapped or wound about wand body 120 so as to form a helical or spiraling electrode structure about wand body 120. Each helical or spiraling electrode structure may be characterized in that each turn is spaced from the adjacent turns of said electrode. In an embodiment, one or more, and preferably all turns of each electrode has a pitch distance greater than zero.

In an embodiment, one or both of primary electrode 204 and counter electrode 206 may comprise without limitation, any one of a flat wire electrode, round wire electrode, flat tube electrode, or round tube electrode. In another embodiment, one or both of primary electrode 204 and counter electrode 206 may be integrally, additively, depositively or otherwise formed in a helical arrangement upon the outer circumferential surface of wand body 120. In one embodiment, each of primary electrode 204 and counter electrode 206 may have a polarity different from the other, or may have respectively alternating polarities.

In the particular embodiment that is illustrated in FIG. 2A, the helically arranged primary electrode 204 and helically arranged counter electrode 206 are spaced substantially parallel to each other and are formed around or wound around the outer circumference of wand body 120 in a spiral or helical configuration. This results in primary electrode 204 and counter electrode 206 being spirally formed around or wound about wand body 120 in an alternating spiral configuration, which alternating spiral configuration includes at least one turn of primary electrode 204 being immediately adjacent to and spaced apart from at least one turn of counter electrode 206. In an embodiment, this may be achieved by winding primary electrode 204 in a plurality of turns or wraps that form a helical or spirally wound primary electrode structure about an outer circumference of wand body 120, and by winding counter electrode 206 in a plurality of turns or wraps that form a helical or spirally wound counter electrode structure about the outer circumference of wand body 120—such that one or more than one turns of primary electrode 204 about the outer circumference of wand body 120 are positioned immediately adjacent to and preferably spaced apart from one or more than one turns of counter electrode 206 about the outer circumference of wand body 120.

In an embodiment, the wraps or turns of either or both of primary electrode 204 and counter electrode 206 about the outer circumference of wand body 120 are equally spaced along a longitudinal axis '1' of wand body 120 (i.e. have substantially a uniform pitch distance)—which has been found to ensure uniform plasma density in the radial direction and/or concentrated plasma density along the vertical axis of the wand, and to provide a consistent thickness coating on the interior surfaces of containers that may have varying diameter along the longitudinal axis '1'.

Primary electrode 204 and counter electrode 206 are electrically conductive. In an embodiment, one or both of electrodes 204, 206 may comprise an aluminum electrode, which may or may not have a thin anodize or dielectric coating. In an embodiment that is more clearly shown in FIG. 2B, one end of primary electrode 204 and one end of counter electrode 206 may be respectively coupled to a power source—for example, fixed match transformer assembly 202.

FIG. 2B shows a cross-section of the electrode assembly 108 comprising probe assembly 108 coupled with fixed match transformer assembly 202.

As shown in detail in FIG. 2B, wand body 120 includes a fluid passageway 122 defined therewithin and formed along a longitudinal axis '1' of wand body 120. Wand body 120 additionally has one or more holes or outlet openings 208 formed thereon, which holes or outlet openings 208 are formed on the outer surface of wand 120 and extend inward up to fluid passageway 122—thereby forming fluid channels that connect fluid passageway 122 with an outer surface of wand 120. It would be understood that precursor gas(es) that are drawn or driven into fluid passageway 122 of wand body 120 can exit said fluid passageway 122 of wand body 120 through the holes or outlet openings 208; and, can accordingly enter interior chamber 106.

As illustrated in FIG. 2B, the arrangement of helical or spiral primary electrode 204 and helical or spiral counter electrode 206, and the positioning of holes or outlet openings 208 respectively along the longitudinal axis '1' of wand body 120 is such that holes or outlet openings 208 are positioned between the adjacently positioned turns or windings of primary electrode 204 and counter electrode 206. In other words one or more holes or outlet openings 208 are positioned between adjacently positioned turns or windings of two electrodes having different/alternating polarities. As a result, when precursor gas(es) passes through fluid passageway 122 and out into interior chamber 106 via the holes or outlet openings 208 that are formed on the external surface of wand body 120, said precursor gas(es) passes between the alternating windings or turns of energized primary electrode 204 and counter electrode 206—resulting in excitation of the precursor gases and disassociation of said precursor gases into plasma which would thereafter interact with or be deposited on the one or more treatment surfaces within interior chamber 106.

In the embodiment illustrated in FIGS. 2A and 2B, wand body 120 mounts into a hub 210, which hub 210 may also comprise an electrical insulative material such as ceramic or plastic, and which hub 210 in turn mounts into lower surface 1024 of interior chamber 106. A sheath 212 may be used to cover part of the wand body 120 to limit the outflow of precursor material or generation of plasma to regions corresponding to an upper portion of wand body 120.

In an embodiment where the primary and counter electrodes 204 and 206 are physically wrapped or wound around an outer circumference of wand body 120, said electrodes 204, 206 may run through hub 210 to electrical connectors 214, 214' that are mounted within fixed match transformer assembly 202 or that are respectively connectable to a power source. In a further embodiment, precursor gas(es) enter probe assembly 118 through holes in hub 210, from where the precursor gas(es) proceeds up a fluid passageway 122 that may be substantially coincident with longitudinal axis '1' of wand body 120, and may thereafter exit wand body 120 and pass into interior chamber 106 via holes or outlet openings 208 formed on wand body 120.

The holes or outlet openings 208 formed on wand body 120 may be sized and placed along the longitudinal axis '1' of wand body 120 to provide a uniform distribution of precursor gas(es) for formation of plasma in the radial direction, and in a desired concentration in the longitudinal direction.

Figure 3:
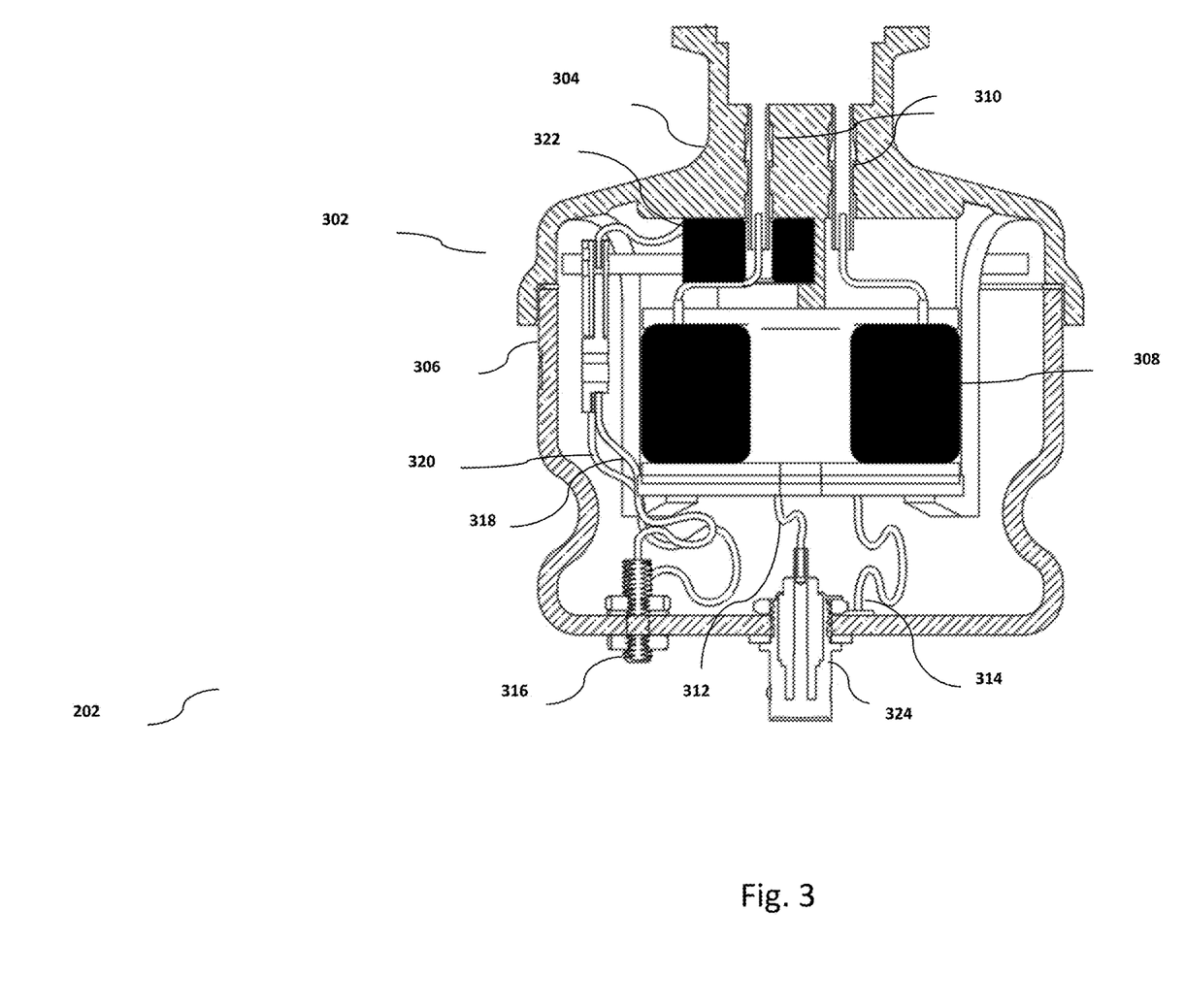
FIG. 3 illustrates an embodiment of a fixed match transformer assembly in accordance with the present invention.

FIG. 3 illustrates an embodiment of fixed match transformer assembly 202. Fixed match transformed assembly 202 comprises an integrated housing assembly 302 having an upper housing 304 and a lower housing 306 which fit together to form an integrated housing assembly for other components of fixed match transformer assembly 202. Each of upper housing 302 and lower housing 304 may comprise plastic material having a conductive coating to provide EMF shielding. Assembled into upper housing 304 is match transformer 308, where the leads of a secondary winding for match transformer 308 terminate to electrical receptacles 310 for electrode leads corresponding to primary electrode 204 and counter electrode 206 of probe assembly 118. Assembled into the lower housing 306 is a 50Ω BNC-type connector with leads 312 and 314 to provide power and ground, respectively, that connect to a primary winding of match transformer 308. In a preferred embodiment, the secondary winding that is terminated to the electrical receptacles 310 communicate in opposing fashion with a floating ground. Also assembled into lower housing 306 is an SMB-type connector 316 with leads 318 and 320 that connect to a positive plug and ground connection for a current transformer 322. When power is applied via a 50 connector 324 to the primary winding of match transformer 308, the secondary winding delivers stepped up voltage to the plasma chamber, when the plasma strikes, current flows and is detected by the current transformer 322 which sends a positive signal via the SMB connector 316.

Figure 4A:
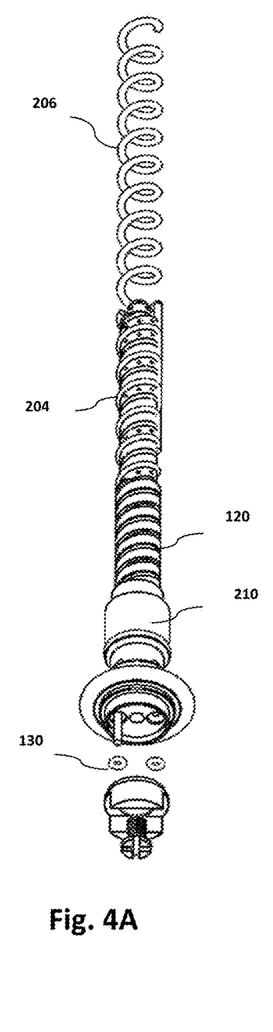
FIG. 4A is an exploded view of a probe assembly in accordance with the present invention.

FIG. 4A is an exploded illustration of probe assembly 118 in accordance with an embodiment of the present invention. As shown in FIG. 4A, probe assembly 118 comprises wand body 120 having helical primary electrode 204 and helical counter electrode 206 respectively wound about an external surface of wand body 120—so as to provide alternating power to dissociate precursor gas(es) and generate plasma. As shown in FIG. 4A, each electrode 204, 206 may be physically wrapped or wound in a spiral or helical configuration about wand body 120, while maintaining a predetermined spacing between alternating turns or windings of electrodes 204, 206 to shape the plasma energy. The end of each electrode 204, 206 passes through hub 210 and a vacuum seal may additionally be formed using one or more O-rings 130.

Figure 4B:
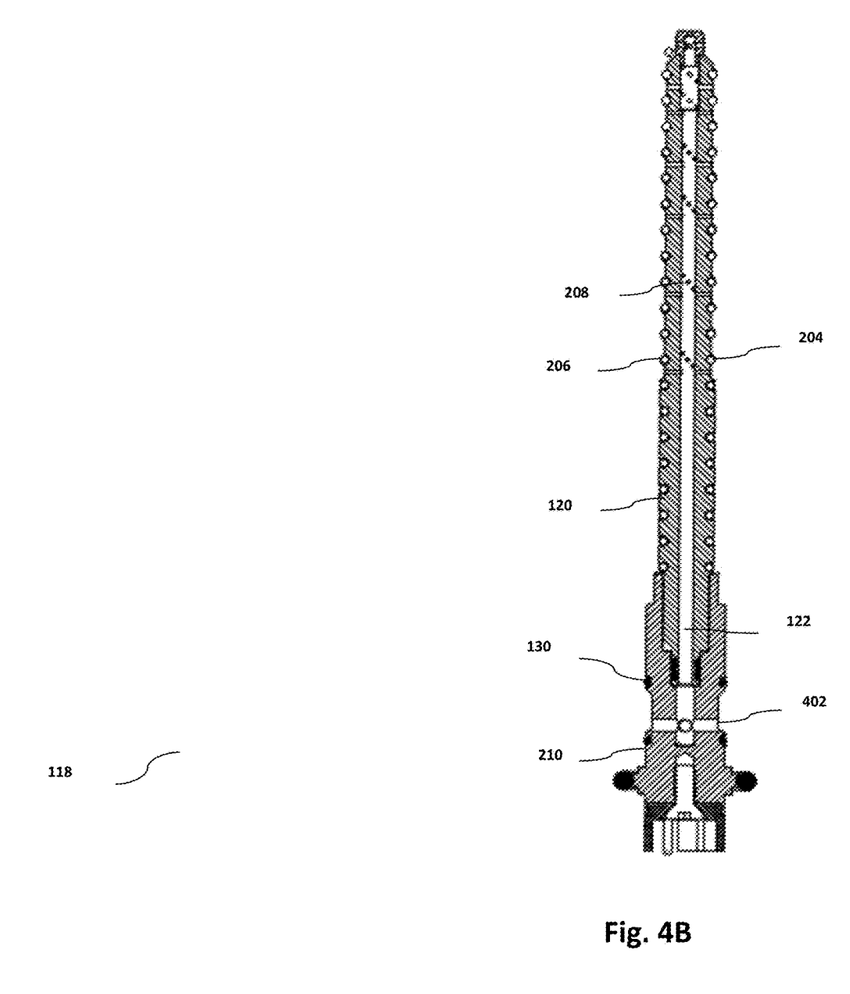
FIGS. 4B and 4C are illustrated cross-sections of probe assemblies in accordance with the present invention.

FIG. 4B is an illustrated cross-section of a probe assembly 118, illustrating the gas path, in accordance with an embodiment of the invention. As shown in FIG. 4B, wand body 120 may be seated in hub 210, and a fluid tight seal may be formed therebetween using one or more O-rings 130. When hub 210 is inserted into a manifold formed on or within a chamber housing (not shown) precursor gas(es) will pass through holes 402 and travel through the fluid passageway 122 defined or formed within wand body 120. The O-ring 130 based fluid tight seal/gas seal formed between hub 210 and wand body 120 prevents precursor gas(es) from escaping through hub 210, thereby ensuring that precursor gas(es) enters wand body 120 and passes through fluid passageway 122 into interior chamber 106 through holes or outlet openings 208 that are located between the alternating windings or turns of electrodes 204 and 206. As discussed above, holes or outlet openings 208 may be placed along wand body 120 in a configuration optimized to obtain a uniform gas concentration and plasma density in the radial direction, while simultaneously having a preferred volumetric concentration of gas distribution along a longitudinal axis '1' of wand body 120—so as to obtain a uniform coating thickness as the active gases are evacuated out of interior chamber 106.

Figure 4C:
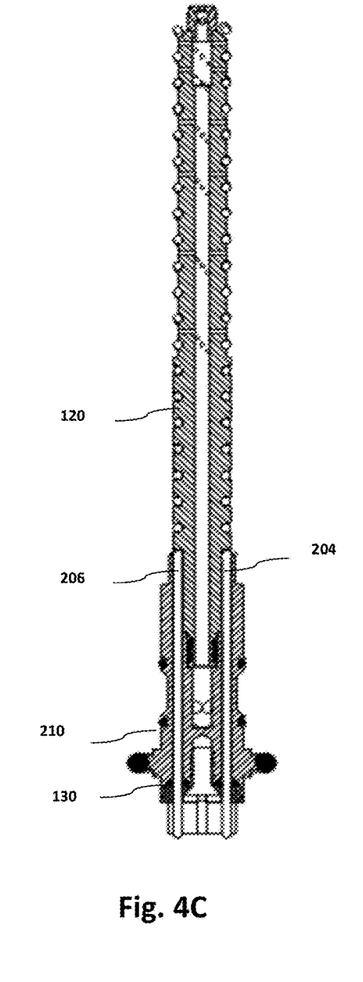

FIG. 4C is an illustrated cross-section of an embodiment of probe assembly 118 in accordance with the present invention—showing the electrode path. It will be noted that the cross section of FIG. 4C is rotated 45° from the cross-section of FIG. 4B. As shown in FIG. 4C, the wand body 120 is seated in hub 210. Electrodes 204 and 206 that are passing through hub 210, are electrically isolated from each other by the material of hub 210—which could typically comprise ceramic or plastic, with a gas seal/vacuum seal formed between each electrode 204, 206 and hub 210, for example using one or more O-rings 130.

Figure 5:
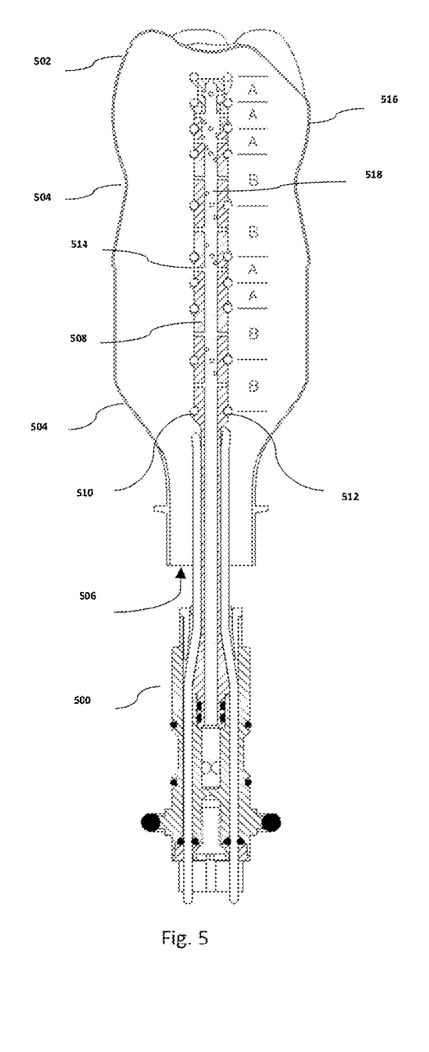
FIG. 5 illustrates an alternate implementation of a probe assembly in accordance with the teachings of the present invention.

FIG. 5 illustrates an alternate embodiment of a probe assembly 500 in accordance with the teachings of the present invention.

The illustration of FIG. 5 shows a cross section of an alternate embodiment probe assembly 500 that may be used to treat internal surfaces of a container 516. Probe assembly 500 comprises a wand body 508 having helically wound primary electrode 510 and helically wound counter electrode 512 that are respectively wound about an outer surface of wand body 508, and arranged in an alternating configuration about the outer circumference of wand body 508, which alternating configuration includes at least one turn of primary electrode 510 being immediately adjacent to (and preferably spaced apart from) at least one turn of counter electrode 512.

In the embodiment of FIG. 5, helical windings of said electrodes 510 and 512 have a varying pitch or varying pitch distance (i.e. varying spacing between turns) measured along a longitudinal axis of wand body 508, to provide varying plasma density at different regions of interior surfaces of container 516, for uniform deposition. As shown in FIG. 5, the primary electrode 510 and counter electrode 512 are helically wound and spaced such that their adjacent turns are separated at a distance "A" in some regions of wand body 508 and at a distance "B" in other regions of wand body 508. This allows for increased energy in regions of the bottle that require additional energized species in those regions to obtain a uniform film deposition on the interior surface of the container 516, while providing a uniform energy in the radial direction. As precursor gas(es) enters the container 516, and is energized and disassociated, it will recirculate with lower velocity near the closed end 502 of container 516. The gases will also have higher velocity at regions of the container that have relatively smaller diameters 504 (for example, smaller than the diameter at closed end 502, or smaller than the diameter at any other region within container 516). Additionally, since all gases will exit container 516 through the annulus 506 created between the mouth of container 516 and probe assembly 500 that has been inserted into container 516 through annulus 506, there can be a heavy build-up of material deposition as reactants have more opportunity to recombine and deposit on the interior surfaces of that region. By varying the pitch of helical windings of said electrodes 510 and 512 along the longitudinal axis of wand body 508, the embodiment of FIG. 5 can be configured to provide varying plasma density at different regions of interior surfaces of container 516, to ensure uniform deposition of plasma on container surfaces despite the existence of one or more than one of the above factors that typically contribute to non-uniform plasma deposition.

Further as illustrated in FIG. 5, holes or outlet openings 514 are formed on wand body 508 for enabling passage of precursor gas(es) from fluid passageway 518 formed within wand body 508 to an interior cavity defined by container 516. In the embodiment illustrated in FIG. 5, said holes or outlet openings 514 are formed with varying spacing, in a manner consistent with the spacing between adjacent turns or windings of the opposing electrodes 510 and 512. This arrangement has been found to allow for higher regions of volumetric flow rate in the different regions along the longitudinal axis of wand body 508. It has additionally been found that differing regions of volumetric flow rate in different regions along the longitudinal axis of wand body 508 can also be accomplished by varying the size of holes or outlet openings 514 size for each of the different regions. The combination of these features has been found to enable more uniform deposition at higher pressures than are typically observed.

In addition to the above, the invention provides methods for manufacturing a probe assembly for an apparatus for treating surfaces of a container, wherein the apparatus comprises an electrode assembly, an openable reaction chamber housing defining an interior vacuum chamber configured to house a container to be treated, and an exhaust escapement configured to permit gases to exit the interior vacuum chamber, and wherein the electrode assembly comprising the probe assembly coupled with a power source. Manufacturing the probe assembly requires providing an elongate wand body having a fluid passageway defined therewithin, the elongate wand body having one or more outlet openings that are formed on an outer circumferential surface of the wand body and that extend inward through said outer circumferential surface and upto the fluid passageway.

A helically configured primary electrode is disposed about the outer circumferential surface of the wand body and having a first plurality of turns, wherein one or more of the first plurality of turns is spaced apart from each immediately adjacent turn within the first plurality of turns.

A helically configured counter electrode is disposed about the outer circumferential surface of the wand body and having a second plurality of turns, wherein one or more of the second plurality of turns is spaced apart from each immediately adjacent turn within the second plurality of turns; and One or more electrical connectors for connecting one or both of the said electrodes to a power source are provided on each of the primary electrode and the counter electrode.

The primary electrode and the counter electrode are disposed about the outer circumferential surface of the wand body in an alternating helical configuration such that one or more turns of the primary electrode are formed immediately adjacent and spaced apart from one or more turns of the counter electrode.

In an embodiment, disposing any one of the helically configured primary electrode or the helically configured counter electrode about the outer circumferential surface of the wand body may comprise winding or otherwise affixing any one of a flat wire electrode, round wire electrode, flat tube electrode, or round tube electrode or other electrode that is in a helical arrangement about the wand body.

In another embodiment, disposing any one of the helically configured primary electrode or the helically configured counter electrode about the outer circumferential surface of the wand body may comprise integrally, additively, depositively or otherwise forming an electrode in a helical arrangement upon the outer circumferential surface of the wand body.

In one embodiment of the method disposing the part of the primary electrode about the outer circumferential surface of the wand body in a helical configuration comprises disposing said part of the primary electrode about the outer circumferential surface of the wand body with a constant pitch across the wand body.

In another embodiment of the method disposing the part of the counter electrode about the outer circumferential surface of the wand body in a helical configuration comprises disposing said part of the counter electrode about the outer circumferential surface of the wand body with a constant pitch across the wand body; or In yet another embodiment disposing the part of the primary electrode about the outer circumferential surface of the wand body in a helical configuration comprises disposing said part of the primary electrode about the outer circumferential surface of the wand body with a varying pitch across the wand body.

In an alternate embodiment, disposing the part of the counter electrode about the outer circumferential surface of the wand body in a helical configuration comprises disposing said part of the counter electrode about the outer circumferential surface of the wand body with a varying pitch across the wand body.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclose herein suitably may be practiced in the absence of any element which is not specifically disclosed herein—and in a particular embodiment that is specifically contemplated, the invention is intended to be practiced in the absence of any one or more element which are not specifically disclosed herein.

What is claimed is:

1. An apparatus for treating surfaces of a container comprising:
    an openable reaction chamber housing defining an interior vacuum chamber configured to house a container for treatment of surfaces of the container;
    an exhaust escapement configured to permit gases to exit the interior vacuum chamber; and
    an electrode assembly configured for coupling with a power source, and positioned at least partially within the interior vacuum chamber, such that a part of the electrode assembly is positioned within an interior cavity of the container housed within the interior vacuum chamber, the electrode assembly comprising:
        a probe assembly coupled with the power source, the probe assembly comprising:
            an elongate wand body, formed from electrically insulative material, having a fluid passageway defined therewithin, and one or more outlet openings that are formed on an outer circumferential surface of the wand body that is formed from the electrically insulative material and that extend inward through said outer circumferential surface and upto the fluid passageway;
            a helically configured primary electrode, formed from electrically conductive material, disposed about the outer circumferential surface of the wand body and having a first plurality of turns, wherein one or more of the first plurality of turns is spaced apart from each immediately adjacent turn within the first plurality of turns; and
            a helically configured counter electrode, formed from electrically conductive material, disposed about the outer circumferential surface of the wand body and having a second plurality of turns, wherein one or more of the second plurality of turns is spaced apart from each immediately adjacent turn within the second plurality of turns;
        wherein:
            the fluid passageway within the wand body is coupled with an inlet manifold and defines a passage between the inlet manifold and the one or more outlet openings that are formed on an outer circumferential surface of the wand body for delivering one or more precursor gases from a precursor gas source through the inlet manifold upto said one or more outlet openings and into the interior vacuum chamber or the interior cavity of the container housed within the interior vacuum chamber;
            the wand body that defines the fluid passageway connecting the inlet manifold and the one or more outlet openings is formed from electrically insulative material that is distinct from the electrically conductive material of the primary electrode and the counter electrode;
            the primary electrode and the counter electrode are disposed about the outer circumferential surface of the wand body in an alternating helical configuration such that one or more turns of the first plurality of turns of the primary electrode are formed immediately adjacent and spaced apart from one or more turns of the second plurality of turns of the counter electrode;
            one or both of the primary electrode and the counter electrode are energizable by the power source; and
            one or more of the outlet openings are formed on the outer circumferential surface of the wand body such that, in entering the interior vacuum chamber or the interior cavity of the container housed within the interior vacuum chamber through said one or more outlet openings, the one or more precursor gases, after exiting through said one or more outlet openings, pass between: i. one or more turns of the first plurality of turns, and, ii. one or more turns of the second plurality of turns.

2. The apparatus as claimed in claim 1, wherein at least a part of the primary electrode and at least a part of the counter electrode are substantially parallel to each other about the outer circumferential surface of the wand body in a helical configuration.

3. The apparatus as claimed in claim 1, wherein a plurality of turns of the first plurality of turns of the primary electrode are formed immediately adjacent to and spaced apart from a corresponding plurality of turns of the second plurality of turns of the counter electrode.

4. The apparatus as claimed in claim 1, wherein the part of the primary electrode that is disposed about the outer circumferential surface of the wand body in a helical configuration has a constant pitch across the wand body.

5. The apparatus as claimed in claim 1, wherein the part of the primary electrode that is disposed about the outer circumferential surface of the wand body in a helical configuration has a varying pitch across the wand body.

6. The apparatus as claimed in claim 1, wherein one or more of the outlet openings are positioned on the outer circumferential surface of the wand body between: i. one or more turns of the first plurality of turns, and, ii. one or more turns of the second plurality of turns.

7. The apparatus as claimed in claim 6, wherein one or more of the outlet openings are positioned on the outer circumferential surface of the wand body between: i. a first turn of the first plurality of turns, and, ii. a second turn of the second plurality of turns, the second turn being immediately adjacent to the first turn.

8. The apparatus as claimed in claim 7, wherein the first and second turns are of different polarities.

9. The apparatus as claimed in claim 1, wherein the primary electrode is one of an anode or a cathode or a ground, and the counter electrode is another of the anode or the cathode or the ground.

10. The apparatus as claimed in claim 1, wherein one or both of the primary electrode and the counter electrode each comprise:
   any one of a flat wire electrode, round wire electrode, flat tube electrode, or round tube electrode or other electrode that is wound or otherwise affixed in a helical arrangement about the wand body.

11. The apparatus as claimed in claim 1, wherein the part of the counter electrode that is disposed about the outer circumferential surface of the wand body in a helical configuration has a constant pitch across the wand body.

12. The apparatus as claimed in claim 1, wherein the part of the counter electrode that is disposed about the outer circumferential surface of the wand body in a helical configuration has a varying pitch across the wand body.

13. The apparatus as claimed in claim 1, wherein the primary electrode and the counter electrode have different polarities.

14. The apparatus as claimed in claim 1, wherein the primary electrode and the counter electrode have alternating polarities.

15. The apparatus as claimed in claim 1, wherein one or both of the primary electrode and the counter electrode are integrally, additively, depositively or otherwise formed in a helical arrangement upon the outer circumferential surface of the wand body.

16. The apparatus as claimed in claim 1, wherein:
   the part of the primary electrode that is helically disposed about the outer circumferential surface of the wand body has a varying pitch across the wand body;
   the part of the counter electrode that is helically disposed about the outer circumferential surface of the wand body has a varying pitch across the wand body; and
   the one or more outlet openings are formed on the outer circumferential surface of the wand body with varying spacing that conforms to the spacing between adjacent turns or windings of the primary electrode and the secondary electrode.

\* \* \* \* \*